(12) United States Patent
Al-Rashdan

(10) Patent No.: US 10,045,775 B1
(45) Date of Patent: Aug. 14, 2018

(54) ARTERIAL CLOSING DEVICE AND METHOD

(71) Applicant: Ibrahim Al-Rashdan, Safat (KW)

(72) Inventor: Ibrahim Al-Rashdan, Safat (KW)

( * ) Notice: Subject to any disclaimer, the term of this patent is extended or adjusted under 35 U.S.C. 154(b) by 0 days.

(21) Appl. No.: 15/944,724

(22) Filed: Apr. 3, 2018

Related U.S. Application Data

(60) Provisional application No. 62/484,338, filed on Apr. 11, 2017.

(51) Int. Cl.
| | |
|---|---|
| *A61B 17/04* | (2006.01) |
| *A61B 17/062* | (2006.01) |
| *A61B 17/06* | (2006.01) |
| *A61M 25/00* | (2006.01) |
| *A61M 25/09* | (2006.01) |
| *A61B 90/00* | (2016.01) |

(52) U.S. Cl.
CPC ........ *A61B 17/0469* (2013.01); *A61B 17/062* (2013.01); *A61B 17/06066* (2013.01); *A61B 2090/3966* (2016.02); *A61M 25/005* (2013.01); *A61M 25/09* (2013.01); *A61M 2025/0004* (2013.01)

(58) Field of Classification Search
CPC .............. A61B 17/0483; A61B 17/062; A61B 17/0491; A61B 17/06066; A61B 17/04; A61B 17/0469; A61B 17/0482; A61B 2017/047
See application file for complete search history.

(56) References Cited

U.S. PATENT DOCUMENTS

| | | | |
|---|---|---|---|
| 5,810,884 A | 9/1998 | Kim | |
| 7,029,480 B2 | 4/2006 | Klein | |
| 7,041,119 B2 | 5/2006 | Green | |
| 8,137,364 B2 | 3/2012 | Zung | |
| 8,636,715 B2 | 1/2014 | Patel | |
| 9,248,256 B2 | 2/2016 | Takagi | |
| 9,301,795 B2 | 4/2016 | Fischell | |
| 2010/0145366 A1* | 6/2010 | Roop ................. | A61B 17/0057 606/144 |
| 2015/0105805 A1* | 4/2015 | Fortson .............. | A61B 17/0469 606/144 |

* cited by examiner

*Primary Examiner* — Diane Yabut
(74) *Attorney, Agent, or Firm* — Richard C. Ltman

(57) ABSTRACT

An arterial closure device includes an elongated catheter having a proximal end, an opposing flexible distal end, and a lumen extending between the proximal end and the distal end. An externalization needle and an internal catheter are disposed within the lumen. The externalization needle is in communication with a first plunger. A first threading needle and a second threading needle are positioned in separate threading channels and in communication with a second plunger. A suture has a first end attached to the second end of the first threading needle and a second end attached to the second end of the second threading needle. A primary aperture extends through a wall of the elongated catheter. A first threading aperture and a second threading aperture extend through the wall of the elongated catheter at opposing sides of the primary aperture.

19 Claims, 6 Drawing Sheets

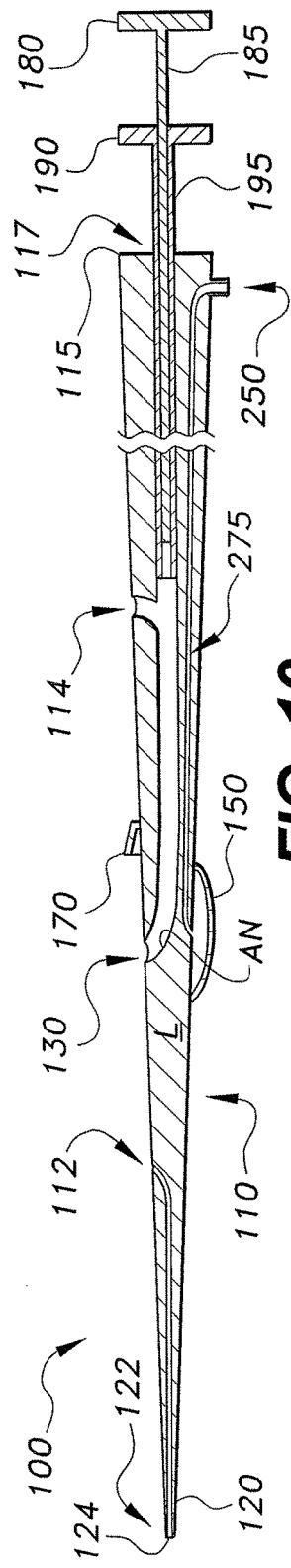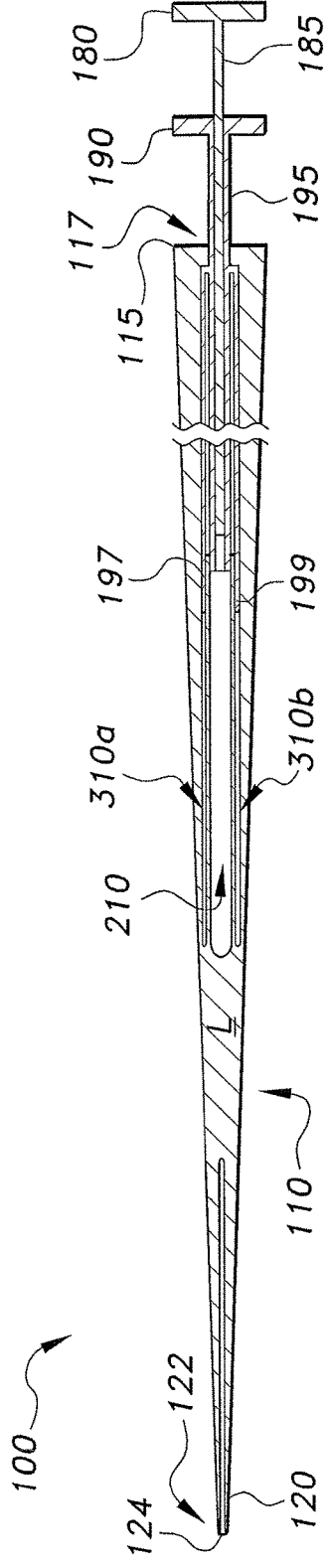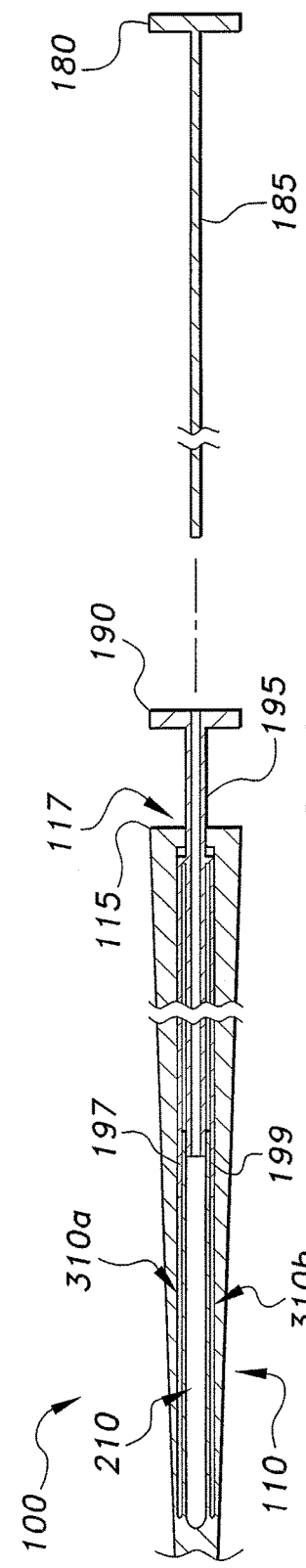

ARTERIAL CLOSING DEVICE AND METHOD

CROSS-REFERENCE TO RELATED APPLICATION

This application claims the benefit of U.S. Provisional Patent Application Ser. No. 62/484,338, filed Apr. 11, 2017.

BACKGROUND

1. Field

The arterial closing device and method relates to an arterial closing device and, particularly to a device for percutaneously closing an arterial access site using needles which puncture the arterial wall anteriorly prior to puncturing the skin.

2. Description of the Related Art

Medical procedures requiring the introduction of a catheter into a blood vessel, such as the femoral or iliac artery, are well known in the art. Such procedures involve piercing the wall of the blood vessel, inserting an introducer sheath into the opening in the blood vessel, and maneuvering the catheter through the sheath to a target site within the blood vessel. At the conclusion of the procedure, it is necessary to seal the opening in the wall of the blood vessel.

One technique utilized to seal the opening in the wall of the blood vessel includes stitching around the opening to suture the opening after the percutaneous intervention is completed to gain homeostasis. The stitching technique is very difficult since its success is dependent on gaining access to the artery by a needle, such as via the Seldinger technique, where the operator punctures the artery blindly from the skin using pulsation as a guide. The success of the stitching technique depends on the positioning of the stitch within the artery. Since the position of the stitching can never be assured, the operator cannot know whether the stitch is centralized, whether the stitch is in a lateral aspect, or whether the stitch is in a small branch of the blood vessel.

Thus, an arterial closure device and method solving the aforementioned problems is desired.

SUMMARY

An arterial closure device includes an elongated catheter having a proximal end, an opposing flexible distal end, and a lumen extending between the proximal end and the distal end. An externalization needle and an internal catheter are disposed within the lumen. The externalization needle is in communication with a first plunger. A first threading needle and a second threading needle are positioned in separate threading channels and in communication with a second plunger. A suture has a first end attached to the second end of the first threading needle and a second end attached to the second end of the second threading needle. A primary aperture extends through a wall of the elongated catheter. A first threading aperture and a second threading aperture extend through the wall of the elongated catheter at opposing sides of the primary aperture.

When depressed, the first plunger drives the externalization needle through the primary channel and out of the primary aperture of the elongated catheter to create a main opening through the arterial wall of the artery and, subsequently, through the skin of the patient. When the second depressible plunger is depressed, each threading needle creates an opening in the arterial wall on either side of the main opening created by the externalization needle.

These and other features of the present invention will become readily apparent upon further review of the following specification and drawings.

BRIEF DESCRIPTION OF THE DRAWINGS

FIG. 10 is a sectional view of the elongated catheter illustrated in FIG. 1.

FIG. 11 is a cut-away view of the elongated catheter.

FIG. 12 is a partial, exploded view of the elongated catheter of FIG. 11.

Similar reference characters denote corresponding features consistently throughout the attached drawings.

DETAILED DESCRIPTION OF THE PREFERRED EMBODIMENTS

Figure 1:
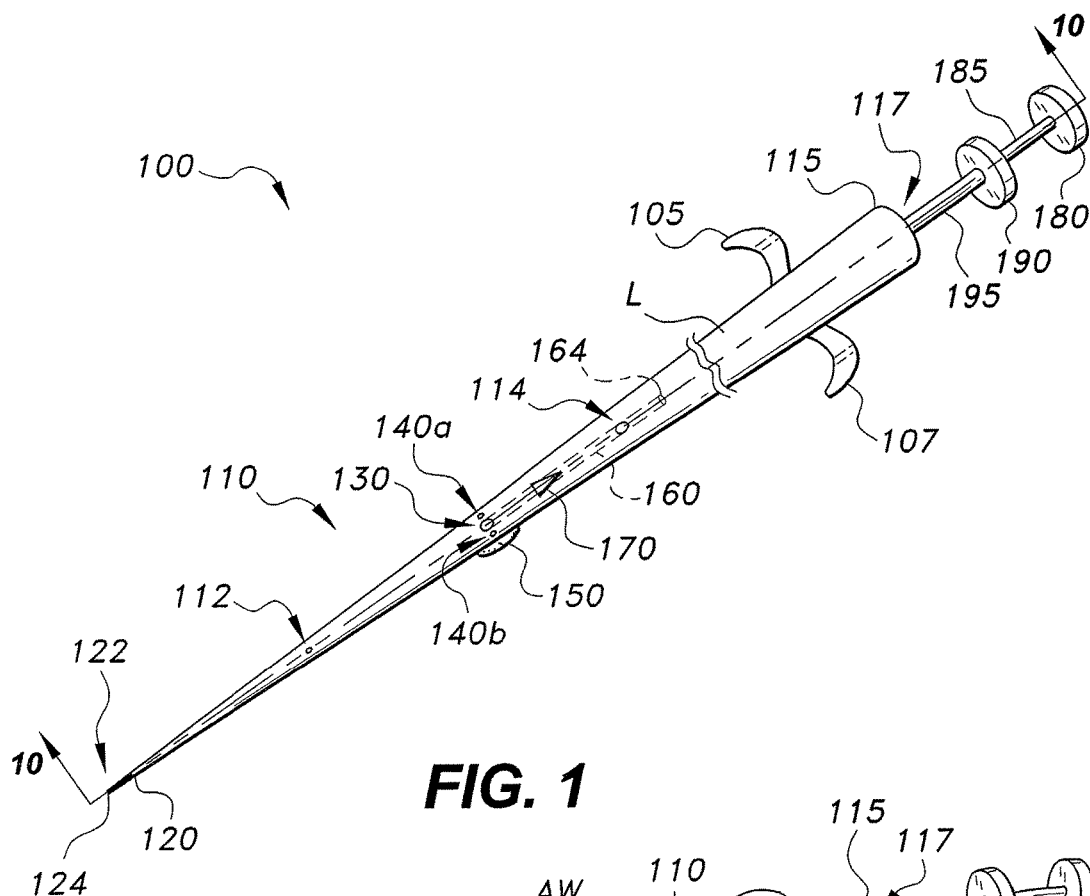
FIG. 1 is a top view of an arterial closing device having an elongated catheter.
Figure 2:
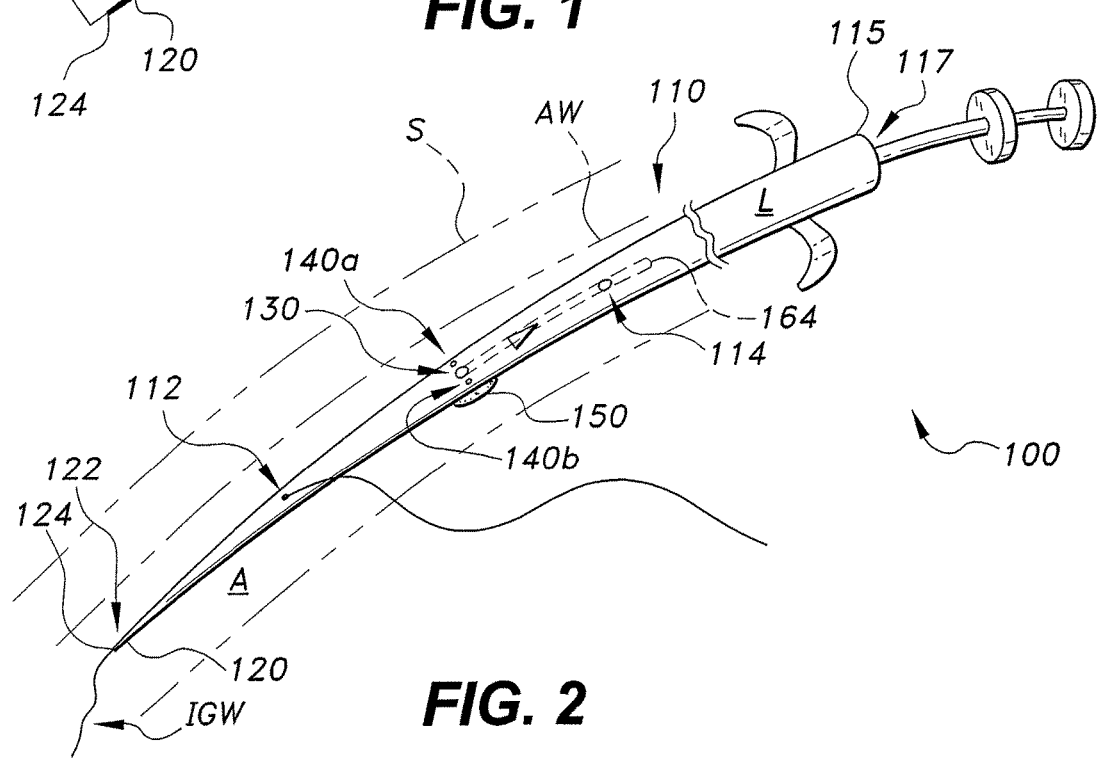
FIG. 2 illustrates the arterial closing device and an introductory guide wire.

Referring to FIGS. 1 through 12, an arterial closure device 100 is generally illustrated. The arterial closure device 100 includes an elongated catheter 110 having a proximal end 115, an opposing flexible distal end 120, and a lumen L extending between the proximal end 115 and the distal end 120. A primary aperture 130 extends through a wall of the elongated catheter 110. A first threading aperture 140a and a second threading aperture 140b extend through the wall of the elongated catheter 110 at opposing sides of the primary aperture 130.

A balloon 150 can be positioned on an outside surface of the elongated catheter 110, below the primary aperture 130 and each secondary aperture 140a, 140b of the elongated catheter 130. The balloon 150 can be connected to a balloon port 250 at the proximal end 115 of the elongated catheter 110 by a balloon channel 275 (FIG. 10). The balloon port 250 is configured for receiving a syringe (not shown), which can be filled with saline for example, to inflate the balloon 150. The balloon 150, once inflated, can stabilize the elongated catheter 110 within an artery A, such as the femoral artery. The balloon can also push the elongated catheter 110, e.g., in an upward direction, against the arterial wall AW.

The primary aperture 130 and the first and second threading apertures 140a and 140b, are between a distal aperture 112 and a proximal aperture 114. The distal aperture 112 is provided proximate the distal end 120 of the elongated catheter 110. The proximal aperture 114 is provided proximate the proximal end 115 of the elongated catheter 110. A portion of the elongated catheter 110, e.g., proximate the primary aperture 130, can include a radiopaque marker to aid in determining the proper placement of the elongated catheter 110 within the artery A. The radiopaque marker can include at least one of barium sulfate, bismuth subcarbonate, bismuth oxychloride, bismuth trioxide, and tungsten.

The arterial closure device 100 further includes an externalization needle 200 and an internal catheter 160 disposed within the lumen L of the elongated catheter 110. The externalization needle 200 is positioned within a primary channel 210 (FIGS. 11 and 12) in the lumen L of the elongated catheter 110. The externalization needle 200 has a first end 205 including a piercing tip and an opposing second end 207. The tip can be used for piercing through the arterial wall AW and the skin S of the patient to create a main opening in the arterial wall AW and the skin S. The internal catheter 160 includes a first opening 162 and an opposing second opening 164.

Figure 7:
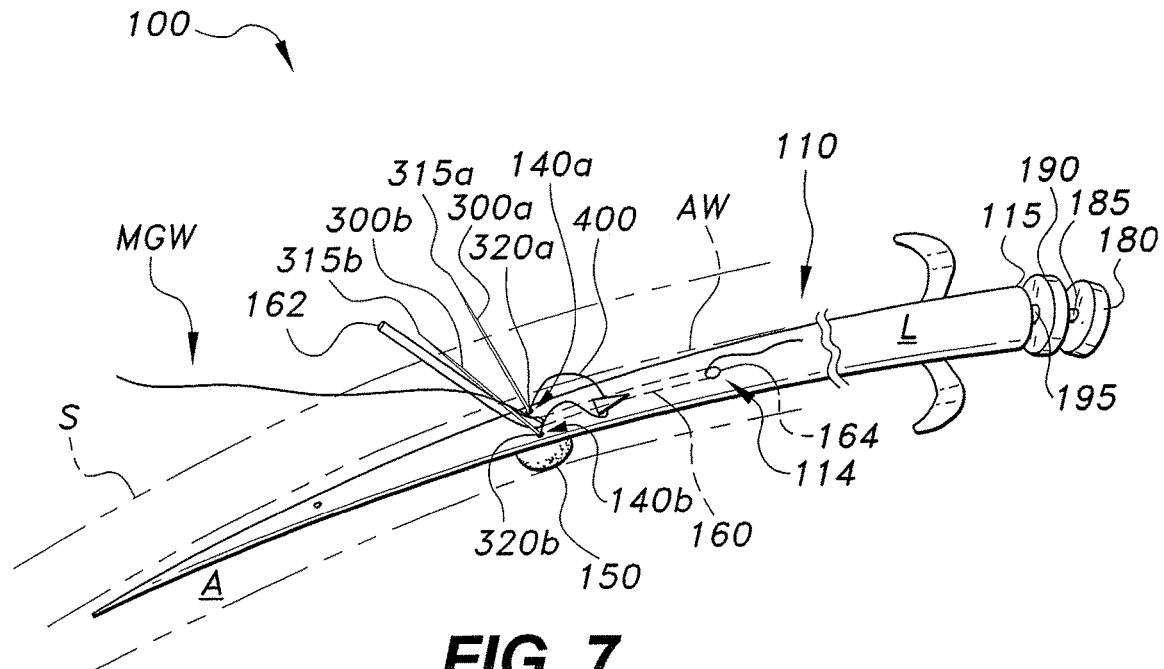
FIG. 7 illustrates a first threading needle and a second threading needle coupled to a suture, the first and second threading needle protruding out of the elongated catheter.
Figure 8:
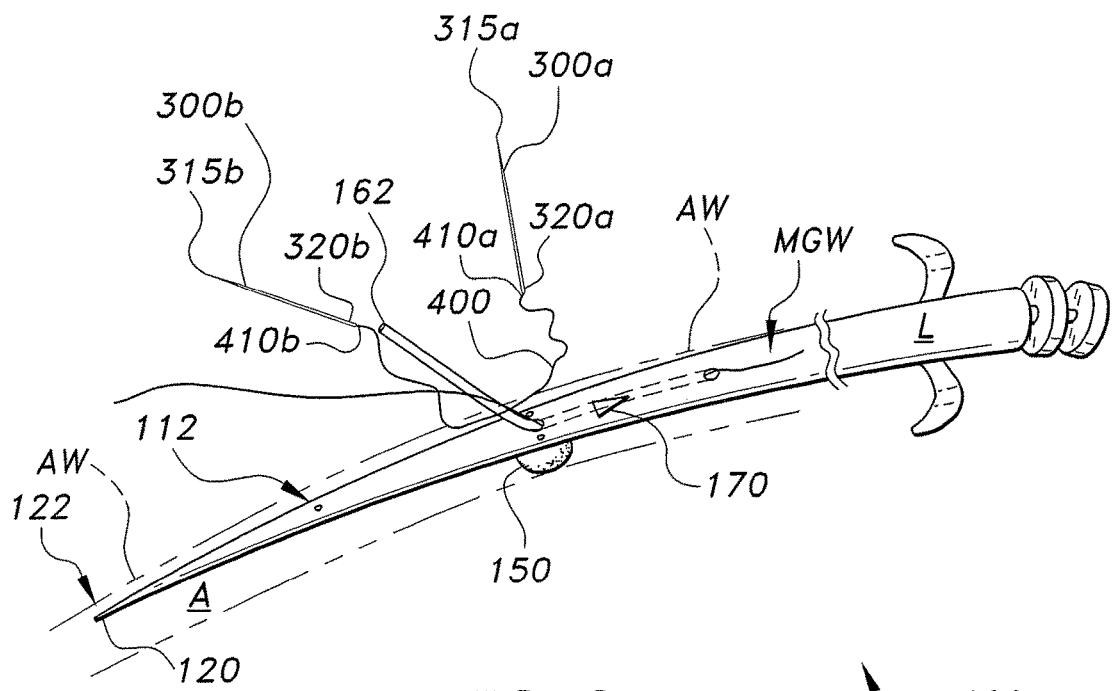
FIG. 8 illustrates the suture removed from the catheter and positioned within the blood vessel.
Figure 9:
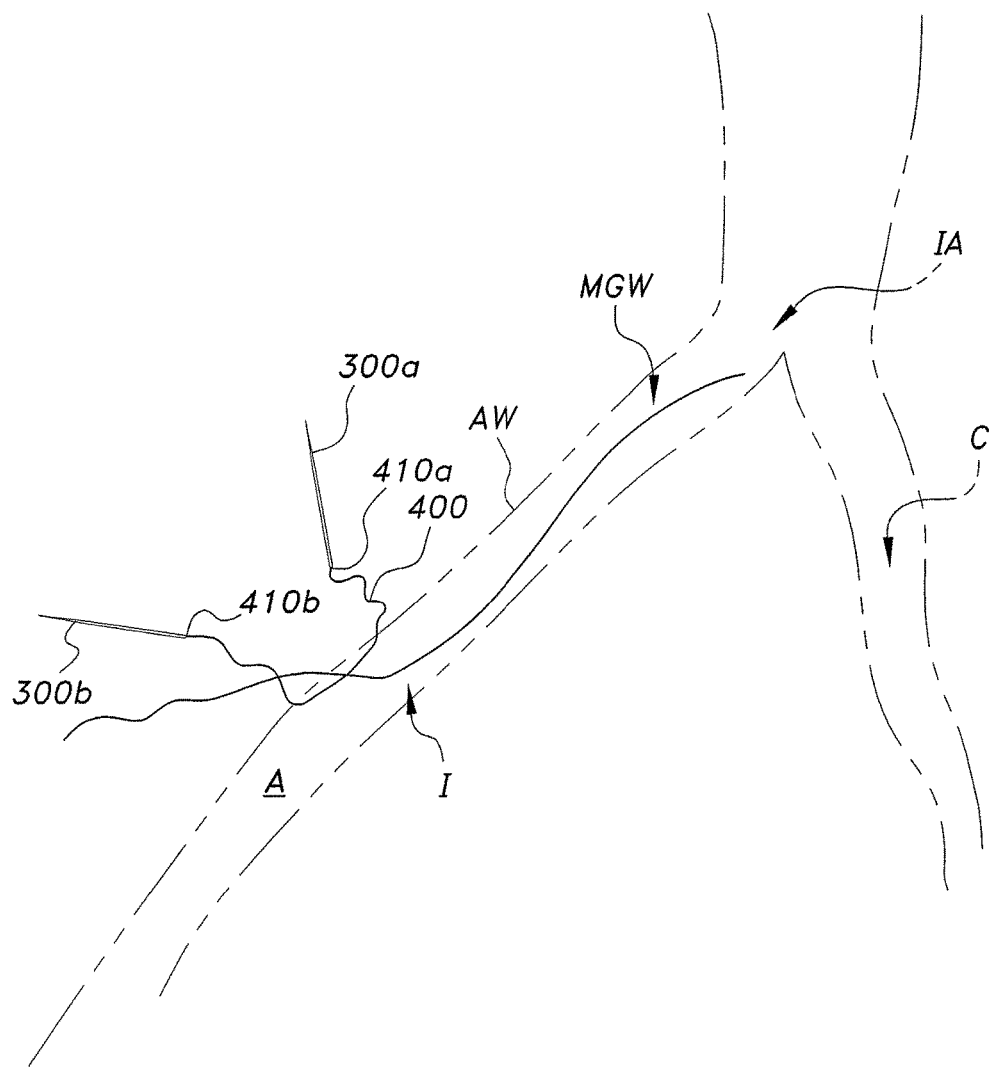
FIG. 9 illustrates the main guide wire positioned within the artery after the elongated catheter of the arterial closing device has been removed.

A first threading needle 300a is positioned within a first threading channel 310a and a second threading needle 300b is positioned within a second threading channel 310b, as illustrated in FIGS. 7, 11, and 12. Threading needles 300a, 300b include a first end, such as tip 315a and 315b, respectively, and an opposing second end, such as opposing end 320a and 320b, respectively. The threading needles 300a, 300b can be pushed through the first threading aperture 140a and the second threading aperture 140b, respectively, for piercing through the arterial wall AW and creating a corresponding opening in the arterial wall AW. The openings created by the first threading needle 300a and the second threading needle 300b can be at opposing sides of the main opening created in the arterial wall by the externalization needle 200.

The distal end 120 of the elongated catheter 110 includes a soft tip 122, such as a soft, arcuate tip, having at least one hole 124 defined therein. The at least one hole 124 is configured for receiving an introductory guide wire IGW. The distal end 120 of the elongated catheter 110 can include a plurality of flexible segments with varying degrees of stiffness to facilitate the elongated catheter 110 through the artery A. The soft tip 122 portion of the elongated catheter 110 can be formed from soft Pebax® or any other type of suitable material.

The proximal end 115 of the elongated catheter 110 includes a port 117 for receiving a first depressible plunger 180 and a second depressible plunger 190, the plungers 180, 190 being independently depressible. The first plunger 180 includes a shaft 185 having a given diameter, while the second plunger 190 includes a hollow shaft 195 having a diameter greater than the given diameter of the first plunger 180. The shaft 185 of the first plunger 180 can be inserted into the hollow shaft 195 of the second plunger 190. The shaft 185 of the first plunger 180 is positioned in communicating relation with the second end 207 of the externalization needle 200. The hollow shaft 195 of the second plunger 190 includes a first prong 197 and a second prong 199, as illustrated in FIGS. 11 and 12. The first prong 197 is positioned in communicating relation with the second end 320a of the first threading needle 300a and the second prong 199 is positioned in communicating relation with the second end 320b of the second threading needle 300b.

The elongated catheter 110 can include a wall of substantially uniform thickness, and first and second finger supports 105, 107 extending from opposing sides of the wall. The supports 105, 107 can be adapted to allow for better control of the arterial closure device 100 while the medical practitioner depresses each plunger 180, 190.

The primary channel 210 and each secondary channel 310a, 310b can be angled, e.g. to form a 45° angle AN, as illustrated in FIG. 10, to guide the externalization needle 200, as well as each threading needle 300a, 300b out of the elongated catheter 110 toward the arterial wall, such as via the primary aperture 130 and the first and second threading apertures 140a, 140b, respectively. Alternatively, the elongated catheter 110 can include a differential balloon to guide the externalization needle 200 as well as each threading needle 300a, 300b toward the arterial wall and out of the elongated catheter 110.

The device 100 includes a suture 400 having a first end 410a attached to the second end 320a of the first threading needle 300a and a second end 410b attached to the second end 320b of the second threading needle 300b. A pocket 170 can be provided on the outer surface of the elongated catheter 110, such as adjacent the primary aperture 130 and each secondary aperture 140a, 140b. The pocket 170 is configured for storing the suture 400 for the threading needles 300a, 300b.

The elongated catheter 110 is adapted for placement in the artery A, such as within the contralateral side C (FIG. 9) of the artery A via an arterial puncture so as to access the ipsilateral side I of the artery A. The elongated catheter 110 can be formed from any type of medical grade material, and is preferably an elongate, flexible tubular structure having a braided construction. The braided construction of the elongated catheter 110 can enhance torqueability, pushability, and kink resistance when being advanced through the artery A, such as from the contralateral side C of the artery A towards the ipsilateral side I of the artery A. The braided portion of the elongated catheter 110 can be formed from a metal, a polytetrafluoroethylene (PTFE) core, and/or a Pebax®. While the elongated catheter 110 can vary in length and French (Fr) size, it is desirable that the elongated catheter 110 have at least a 6 Fr size in diameter and a usable length of at least about 60 cm, such that the elongated catheter 110 can be advanced from the contralateral side C of the artery A to a predetermined position on the ipsilateral side I of the artery A.

Figure 5:
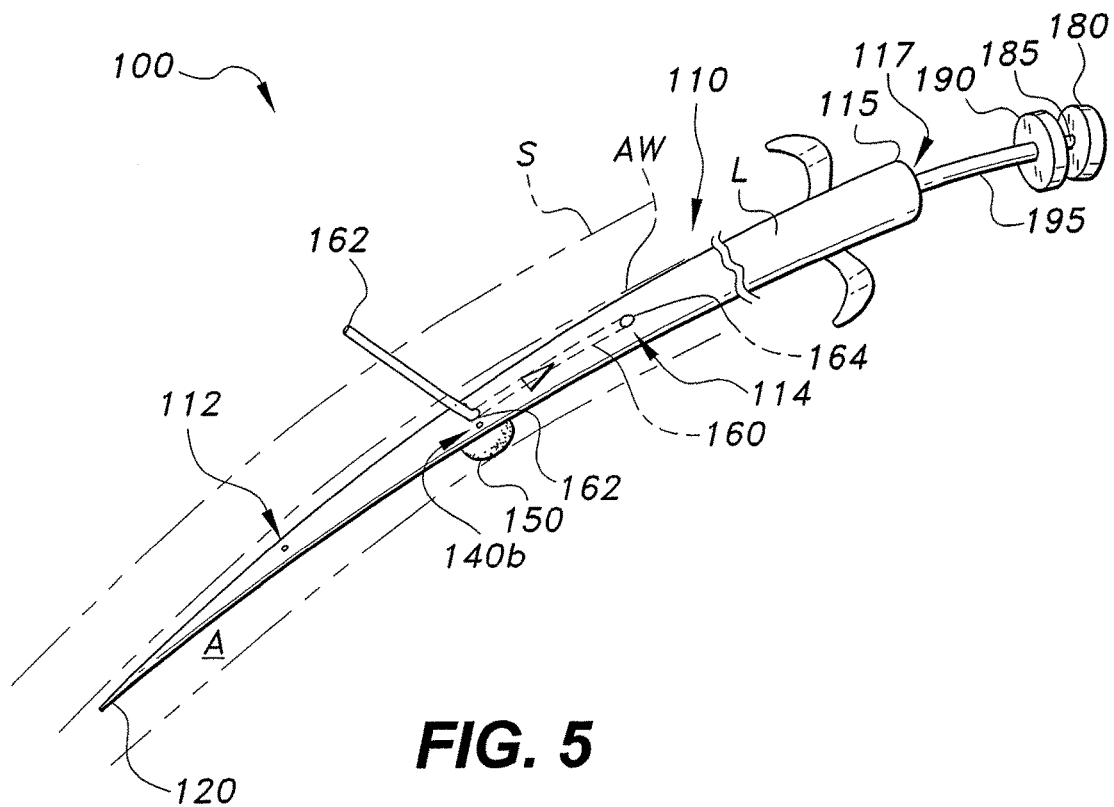
FIG. 5 illustrates the internal catheter extending through the primary opening of the elongate catheter and through the skin of the patient.

When the first plunger 180 is depressed, the shaft 185 of the first plunger 180 drives externalization needle 200 through the primary channel 210 and out of the primary aperture 130 of the elongated catheter 110 to create a main opening (not shown) through the arterial wall AW of the artery A and, subsequently, through the skin S of the patient. As the externalization needle 200 is driven outward through the primary aperture 130 of the elongated catheter 110, the internal catheter 160 is also pulled outward through the primary aperture 130 by the second end 207 of the externalization needle 200. The first opening 162 of the internal catheter 160 can then extend outside of the skin S of the patient, as illustrated in FIG. 5, to serve as a guidewire entry port for receiving a main guide wire MGW. The second opening 164 of the internal catheter 160 may then align with the second aperture 114 of the lumen L, such that the main guidewire MGW can gain access to the artery A that will be used for the medical procedure, such as a cardiac catheterization.

When the second depressible plunger 190 is depressed, each threading needle 300a, 300b is driven through the corresponding secondary channel 310a, 310b and outward through corresponding secondary apertures 140a, 140b of the elongated catheter 110. Each threading needle 300a, 300b creates an opening in the arterial wall AW on either side of the main opening in the arterial wall AW created by the externalization needle 200 from the inside out, similar to the manner in which the externalization needle 200 creates the main opening in the arterial wall AW, described herein.

The externalization needle 200 and each threading needle 300a, 300b can be formed from any suitable material, such as metal. The suture 400 can be any suitable type of suture. Exemplary sutures can include absorbable sutures formed from polyglactin 910 (i.e., vicryl), polyglyconate, polydioxane, or poliglecaprone, or non-absorbable sutures formed from silk, nylon, polyester, polypropylene, or cotton.

By way of operation, prior to commencing a procedure, such as a cardiac catheterization, a medical practitioner makes an incision to access the artery A, such as the femoral artery. Once the medical practitioner makes the incision, s/he inserts the introductory guide wire IGW into the contralateral side C of the artery A and threads the introductory guide wire IGW through the artery A until the introductory guide wire IGW reaches the ipsilateral side I of the artery A for the medical procedure.

After the introductory guide wire IGW reaches the target in the artery A, the introductory guide wire IGW is threaded into the hole 124 at the soft tip 122 of the distal end 120 of the elongated catheter 110 and out of the distal aperture 112 of the lumen L. The elongated catheter 110 is then advanced toward the predetermined position in the ipsilateral side I of the artery A. The medical practitioner can utilize an X-Ray machine, for example, to monitor the position of the elongated catheter 110 as the elongated catheter 110 is being moved.

A contrast agent can be injected into the artery A to determine whether the elongated catheter 110 is properly positioned within the artery A. For example, the contrast agent can be introduced at the proximal end of the elongated catheter 110 via a contrast port (not shown) and removed from the elongated catheter 110 through the primary aperture 130. Once it is determined that the elongated catheter 110 is properly positioned, the balloon 150 can be inflated, such as by attaching a syringe (not shown) to the balloon port 250 and injecting saline into the balloon port 250 and through the channel 275. Inflation of the balloon 150 can centralize the elongated catheter 110 within the artery A and push the elongated catheter 110 upward toward the arterial wall AW.

Figure 3:
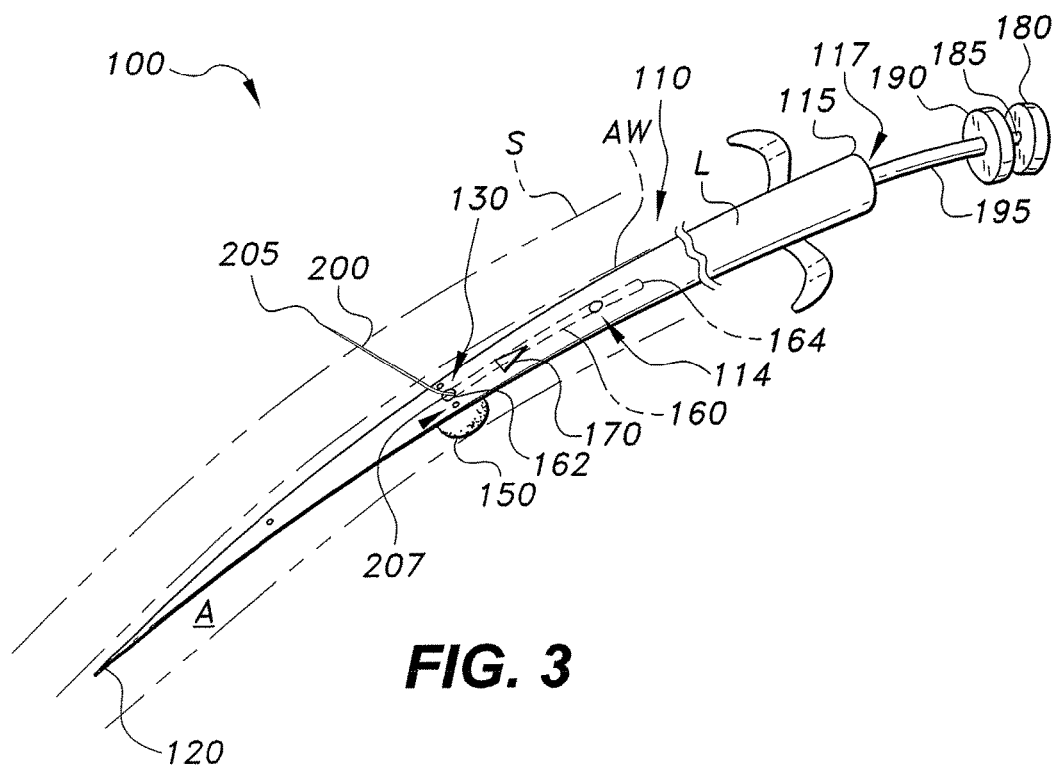
FIG. 3 illustrates an externalization needle coupled to an internal catheter.
Figure 4:
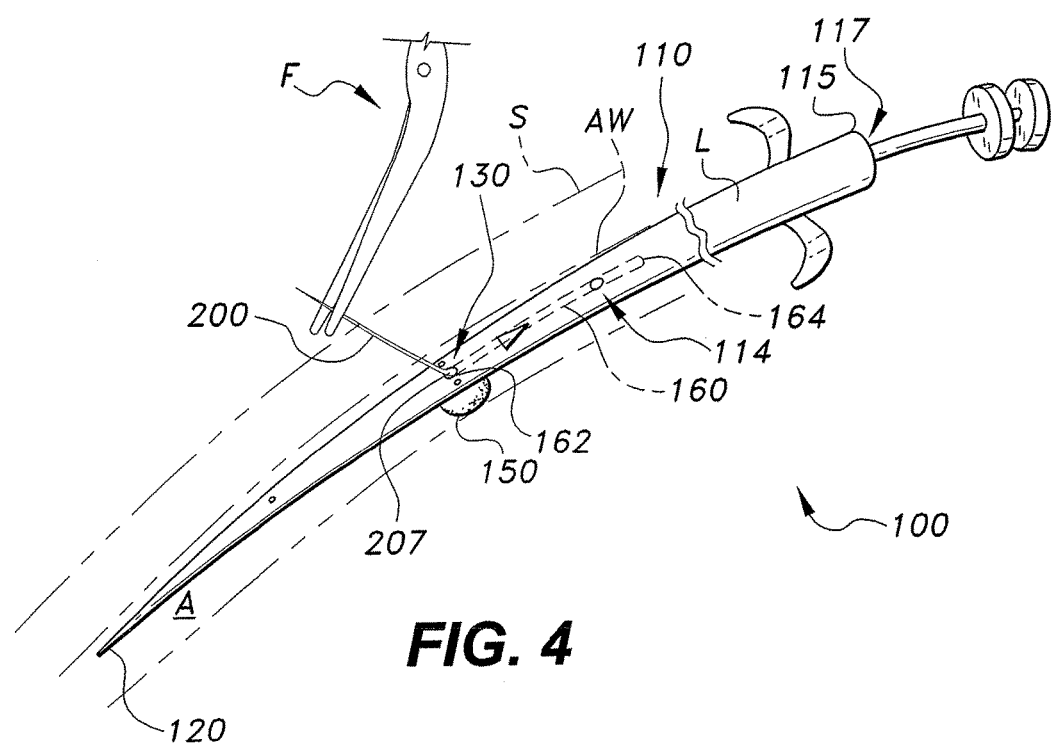
FIG. 4 illustrates a pair of forceps being used to remove the externalization needle once the externalization needle has created a main opening in the wall of a blood vessel and the skin of the patient.

Once the elongated catheter 110 is properly positioned in the artery A, the first depressible plunger 180 can be depressed to drive the externalization needle 200 along the primary channel 210 and through the primary aperture 130 of the elongated catheter 110 to create the main opening, as illustrated in FIG. 3. After the externalization needle 200 creates the main opening (not shown) in the artery A and pierces the skin S of the patient above the opening in the arterial wall AW, the externalization needle 200 can be pulled upward, as illustrated in FIG. 4. The second end 207 of the externalization needle 200 can be separated from the first end 162 of the internal catheter 160 once the internal catheter 160 protrudes from the skin (s) of the patient. Pulling the externalization needle 200 from the patient's skin can cause the first end 162 of the internal catheter 160 to protrude through the main opening in the arterial wall AW as well as the opening in the patient's skin S and cause the second end 164 of the internal catheter 160 to align with the second aperture 114 of the elongated catheter 110.

Figure 6:
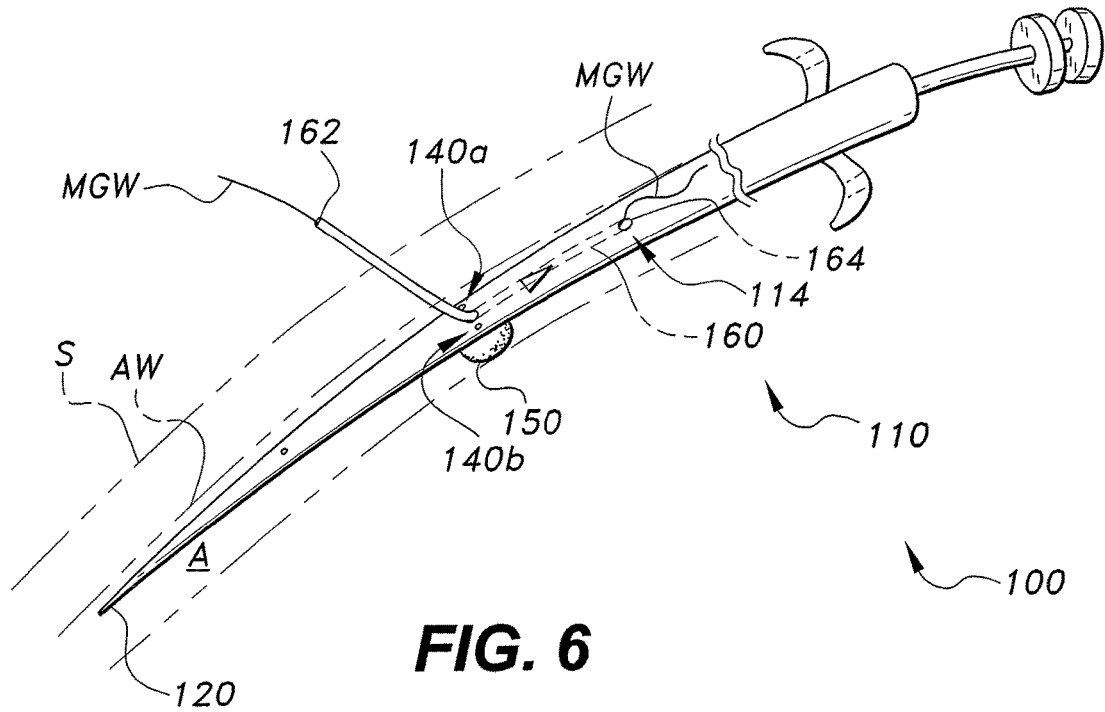
FIG. 6 illustrates a main guide wire being threaded through the internal catheter and into the blood vessel of the patient.

The main guide wire MGW that will be utilized for the medical procedure can then be threaded into the first opening 162 of the internal catheter 160 and out of the opposing second end 164 of the internal catheter 160, as illustrated in FIG. 6. After the main guide wire MGW has been threaded through the internal catheter 160, the internal catheter 160 is removed completely from the elongated catheter 110 and the main guide wire MGW skin entry point is widened, such as by blunt dissection, to allow for the threading needles 300a, 300b to protrude from the same skin opening. Subsequently, the second depressible plunger 190 can be depressed to drive each threading needle 300a, 300b through the corresponding secondary channel 310a, 310b and through each corresponding secondary aperture 140a, 140b of the elongated catheter 110. Once each threading needle 300a, 300b is pushed out of the corresponding secondary aperture 140a, 140b, the threading needles 300a, 300b exit the arterial wall AW, such as on either side of the main opening created in the arterial wall AW by the externalization needle 200, so that both threading needles 300a, 300b are angled to exit the skin S from the same incision made by the externalization needle 200 and widened by the blunt dissection. The threading needles 300a, 300b are then pulled away from the elongated catheter 110 such that the suture 400 is taken out of the pocket 170.

The elongated catheter 110 is then pulled along the main guide wire MGW until the elongated catheter 110 is removed from the contralateral side C of the artery A and the distal aperture 112 is outside of the skin S to allow for rewiring with a second guide wire (not shown) for the contralateral side C. The second guide wire is configured to gain access to the arterial lumen of the contralateral artery through the distal end 120 before the elongated catheter 110 is completely removed. The second guide wire is positioned to allow the insertion of another femoral sheath, such as a regular use 6 Fr femoral sheath, for control purposes and secondary use. After the procedure, the femoral sheath, such as the regular 6 Fr sheath, can be removed and pressure may be applied to the location of the initial incision until homeostasis is achieved. After the elongated catheter 110 is removed, the medical practitioner(s) can commence with the medical procedure, such as by threading a large bore catheter (not shown) along the main guide wire MGW and toward the target location in the heart, for example. At the completion of the medical procedure and once the large bore catheter has been removed, the medical practitioner can grasp each of the threading needles 300a, 300b to stitch the main opening, created in the arterial wall AW by the externalization needle 200.

It is to be understood that the arterial closing device and method is not limited to the embodiments described above, but encompasses any and all embodiments within the scope of the following claims.

I claim:
1. An arterial closing device, comprising:
  an elongated outer catheter including
    a hollow body having a proximal end, a distal end, and a lumen extending from the proximal end to the distal end, the distal end having a flexible tip and at least one hole defined therethrough,
    a primary aperture defined in a wall of the catheter body,
    a first threading aperture defined in the catheter wall along a first side of the primary aperture, and
    a second threading aperture defined in the catheter wall along a second side of the primary aperture;

an internal catheter disposed within the lumen of the elongated outer catheter, the internal catheter including a hollow body having a first opening and an opposing second opening;

a first depressible plunger extending through the proximal end of the elongated outer catheter;

a second depressible plunger extending through the proximal end of the elongated outer catheter, the first depressible plunger being slidably disposed within the second depressible plunger, the first depressible plunger and the second depressible plunger being independently depressible;

an externalization needle removably positioned in a primary channel in the lumen, the externalization needle being in communication with the first plunger;

a first threading needle removably positioned in a first threading channel in the lumen;

a second threading needle removably positioned in a second threading channel in the lumen, the first and second threading needles being in communication with the second plunger; and a suture positioned in communicating relation with the first and second threading needles.

2. The arterial closing device according to claim 1, wherein the elongated outer catheter further comprises a pocket on an outer surface thereof for storing the suture.

3. The arterial closing device according to claim 1, wherein the elongated outer catheter further comprises an inflatable balloon extending from the catheter wall below the primary aperture for lifting the elongated catheter toward the arterial wall of the artery.

4. The arterial closing device according to claim 1, wherein the elongated outer catheter further comprises a first finger support and a second finger support extending from opposite sides of the catheter wall.

5. The arterial closing device according to claim 1, wherein the second depressible plunger includes a first prong and a second prong, the first prong being positioned along one side of the first depressible plunger and the second prong being positioned along an opposite side of the first depressible plunger.

6. The arterial closing device according to claim 1, wherein the suture has a first end attached to the first threading needle and a second end attached to the second threading needle.

7. The arterial closing device according to claim 1, wherein the primary aperture is in communication with the primary channel, the first threading aperture is in communication with the first threading channel, and the second threading aperture is in communication with the second threading channel.

8. The arterial closing device according to claim 1, wherein the internal catheter is in communication with the externalization needle.

9. The arterial closing device according to claim 1, wherein the primary channel, the first threading channel, and the second threading channel are angled.

10. The arterial closing device according to claim 1, wherein the elongated outer catheter further comprises a distal aperture and a proximal aperture defined along a same side of the elongated outer catheter as the primary aperture and the first and second threading apertures.

11. An arterial closing device, comprising:

an elongated outer catheter including a hollow body having a proximal end, a distal end, and a lumen extending from the proximal end to the distal end, the distal end having a flexible tip and at least one hole defined therethrough;

a primary aperture defined in a wall of the catheter body, a first threading aperture defined in the catheter wall along a first side of the primary aperture, and a second threading aperture defined in the catheter wall along a second side of the primary aperture;

a first depressible plunger extending through the proximal end of the elongated outer catheter;

a second depressible plunger extending through the proximal end of the elongated outer catheter, the first depressible plunger being slidably disposed within the second depressible plunger, the first depressible plunger and the second depressible plunger being independently depressible;

an externalization needle removably positioned in a primary channel in the lumen, the externalization needle being in communication with the first plunger;

a first threading needle removably positioned in communication with the first threading aperture;

a second threading needle removably positioned in communication with the second threading aperture, the first and second threading needles being in communication with the second plunger; and a suture positioned in communicating relation with the first and second threading needles.

12. The arterial closing device according to claim 11, wherein the elongated catheter further comprises a pocket on an outer surface thereof for storing the suture.

13. The arterial closing device according to claim 11, wherein the elongated catheter further comprises an inflatable balloon below the primary aperture for lifting the elongated catheter toward the arterial wall of the artery.

14. The arterial closing device according to claim 11, wherein the elongated catheter further comprises a first finger support and a second finger support extending from opposite sides of the catheter wall.

15. The arterial closing device according to claim 11, wherein the second depressible plunger includes a first prong and a second prong, the first prong being positioned along one side of the first depressible plunger and the second prong being positioned along an opposite side of the first depressible plunger.

16. The arterial closing device according to claim 11, wherein the suture has a first end attached to the first threading needle and a second end attached to the second threading needle.

17. The arterial closing device according to claim 11, wherein the elongated outer catheter further comprises an internal catheter including a first opening and an opposing second opening, the internal catheter being positioned in the lumen of the elongated catheter.

18. The arterial closing device according to claim 17, wherein the internal catheter is in communication with the externalization needle.

19. The arterial closing device according to claim 11, further comprising a distal aperture and a proximal aperture defined along a same side of the elongated catheter as the primary aperture and the first and second threading apertures.

\* \* \* \* \*